US006454718B1

United States Patent
Clift

(10) Patent No.: US 6,454,718 B1
(45) Date of Patent: Sep. 24, 2002

(54) INTRA AURAL INTEGRATED VITAL SIGNS MONITOR

(76) Inventor: Vaughan L. Clift, 807 Noble Springs Rd., Houston, TX (US) 77062

( * ) Notice: Subject to any disclaimer, the term of this patent is extended or adjusted under 35 U.S.C. 154(b) by 0 days.

(21) Appl. No.: 09/554,044

(22) PCT Filed: Nov. 5, 1998

(86) PCT No.: PCT/AU98/00924
§ 371 (c)(1),
(2), (4) Date: May 9, 2000

(87) PCT Pub. No.: WO99/23941
PCT Pub. Date: May 20, 1999

(30) Foreign Application Priority Data

Nov. 10, 1997  (AU) ............................................. PP 0309

(51) Int. Cl.⁷ ............................... A61B 5/02; A61B 5/00
(52) U.S. Cl. ........................ 600/483; 600/484; 600/301; 600/559; 600/481; 600/507
(58) Field of Search ................................. 600/300, 301, 600/481, 483, 484, 529, 500, 501, 502, 504, 507, 559, 379

(56) References Cited

U.S. PATENT DOCUMENTS 4,312,358 A * 1/1982 Barney ....................... 600/483
5,673,692 A * 10/1997 Schulze et al. ............. 600/301
6,004,274 A * 12/1999 Nolan et al. ................ 600/486

FOREIGN PATENT DOCUMENTS

DE        3910749 A1 * 10/1990
GB        2210168 A   *  6/1989
GB        2302945 A   *  2/1997
WO   WO-97/009927 A2 *  3/1997

* cited by examiner

Primary Examiner—Kevin Shaver
Assistant Examiner—Navin Natnithithadha
(74) Attorney, Agent, or Firm—Peter A. Borsari

(57) ABSTRACT

An intra aural probe for monitoring multiple physiological parameters simultaneously. The probe includes a pressure sensor, a temperature sensor and a light sensor. The probe is dimensioned to fit snugly and sealingly within the outer aural cavity. The probe measures blood pressure and pulse rate and volume of blood by detecting contraction and expansion in the vascular bed of the lining tissue of the external auditory canal during the cardiac cycle. The probe also measures respiratory rate and respiratory volume by detecting pressure changes across the tympanic membrane or movement of the tympanic membrane induced by corresponding pressure changes in the naso-pharynx and trachea during respiration. In addition, the probe measures temperature in the auditory canal, measures electroencephalographic voltages or electrocardiographic voltages by measuring small potential differences between the external auditory canal region and a suitable reference position, measures electroencephalographic currents by measuring magnetic flux, and measures changes in oxygen saturation of the haemoglobin traveling in the capillary bed lining the external auditory canal.

15 Claims, 2 Drawing Sheets

INTRA AURAL INTEGRATED VITAL SIGNS MONITOR

RELATED APPLICATIONS

This application claims the benefit of priority of PCT International Application No. PCT/AU/00924, filed Nov. 5, 1998, which claims priority from Australian patent application Serial No. PP 0309, filed Nov. 10 1997 in the Australia Patent Office.

FIELD OF INVENTION

The present invention relates to an intra aural probe for monitoring multiple physiological parameters simultaneously. In particular, the intra aural probe, which comprises a pressure sensor, a temperature sensor and a light sensor, is configured to fit snugly and sealinily within the outer aural cavity. Physiological parameters which can be monitored by the intra aural probe of the present invention include blood pressure, pulse rate, and volume of blood, respiratory rate and respiratory volume.

BACKGROUND

There are certain parameters of human physiology that are of great importance for monitoring the well being of a person in many situations. These are; heart rate, blood pressure, respiratory rate, respiratory volume, core temperature and the blood oxygen content sometimes referred to as pulse oximetry. The heart rate is the number of beats per minute and can be measured by counting the pulse at the wrist but is most commonly measured using electrocardiography. This requires electrodes to be placed evenly on three limbs or adjacent portions of the torso. The electrodes cause skin irritation and are subject to electrical noise.

The blood pressure cycles up and down as the heart beats. It is recorded as systolic (upper) and diastolic (lower) pressures during the cycle. Until the development of this method it could only be measured accurately by placing a pressure transducer directly into the artery. An approximate measure could be obtained by placing a semi-inflated cuff around the finger and measuring the added pressure as blood moved into the finger. The latter method is particularly inaccurate when the blood flow to the finger is decreased by cooling the periphery or disease states. An intermittent measurement can be made by inflating a cuff on the upper part of the limb and recording the pressure required to occlude the blood flow in the vessels below. It can not provide a continuous measure. A variant referred to as pulse pressure is the difference between the upper systolic and lower diastolic pressures and can be represented both as a numerical value or a waveform moving from one to the other.

Respiratory rate is the number of breaths per minute and can be measured by counting the expansion and contraction of the chest. It can be monitored continuously using impedance plethysmography, where electrical resistance changes with the volume of the chest. It requires electrodes to be placed on two limbs or either side of the chest. The respiratory volume is the amount of air moved in and out during a breath. The shape of the movement is also valuable information. It can be approximated using the impedance plethysmography but otherwise can only be accurately measured by breathing through a tube into a volume measuring device.

The blood oxygen content is usually measured by infra red spectroscopy. Based on the observation that blood goes from blue to red as it picks up oxygen, the percentage of red blood cell haemoglobin carrying oxygen is calculated from the absorption of different coloured light. The technology is well established in many monitoring situations and is now obligatory during general anaesthesia in most countries. The probe itself is usually applied to the finger but can be clipped to an ear lobe.

Core temperature is a measure of the body's temperature on the central portion such as the heart and brain. Temperature measurements taken in the mouth or axilla are routinely lower and less reliable. During certain situations such as severe dehydration core temperature can increase even when the peripheral temperature does not because of the decreased blood flow to the periphery. Traditionally such core temperature measurement can only be made intermittently using an infra red system applied to the external ear or continuously by placing a temperature probe in the anus.

The technology used in present day modern care facilities requires different measurement systems to be applied to different positions on the body or by the use of very invasive medical devices such as intra arterial catheters and intratracheal tubes. Often these technologies get in the way of the surgeon performing a procedure and severely limit patient mobility and comfort. In certain situations such as monitoring a fighter pilot or a patient during transport, these systems are detrimentally effected by the movement and vibration or simply can not be applied.

In addition, these devices are trying to measure the state of oxygen delivery to the brain, the organ most sensitive to loss of blood flow or oxygenation of the blood. The technology presently used does not measure the supply going to the brain itself and therefore can at best make assumptions based on the activity of the heart and lung and the blood oxygen in other vessels.

DESCRIPTION OF THE INVENTION

Figure 1:
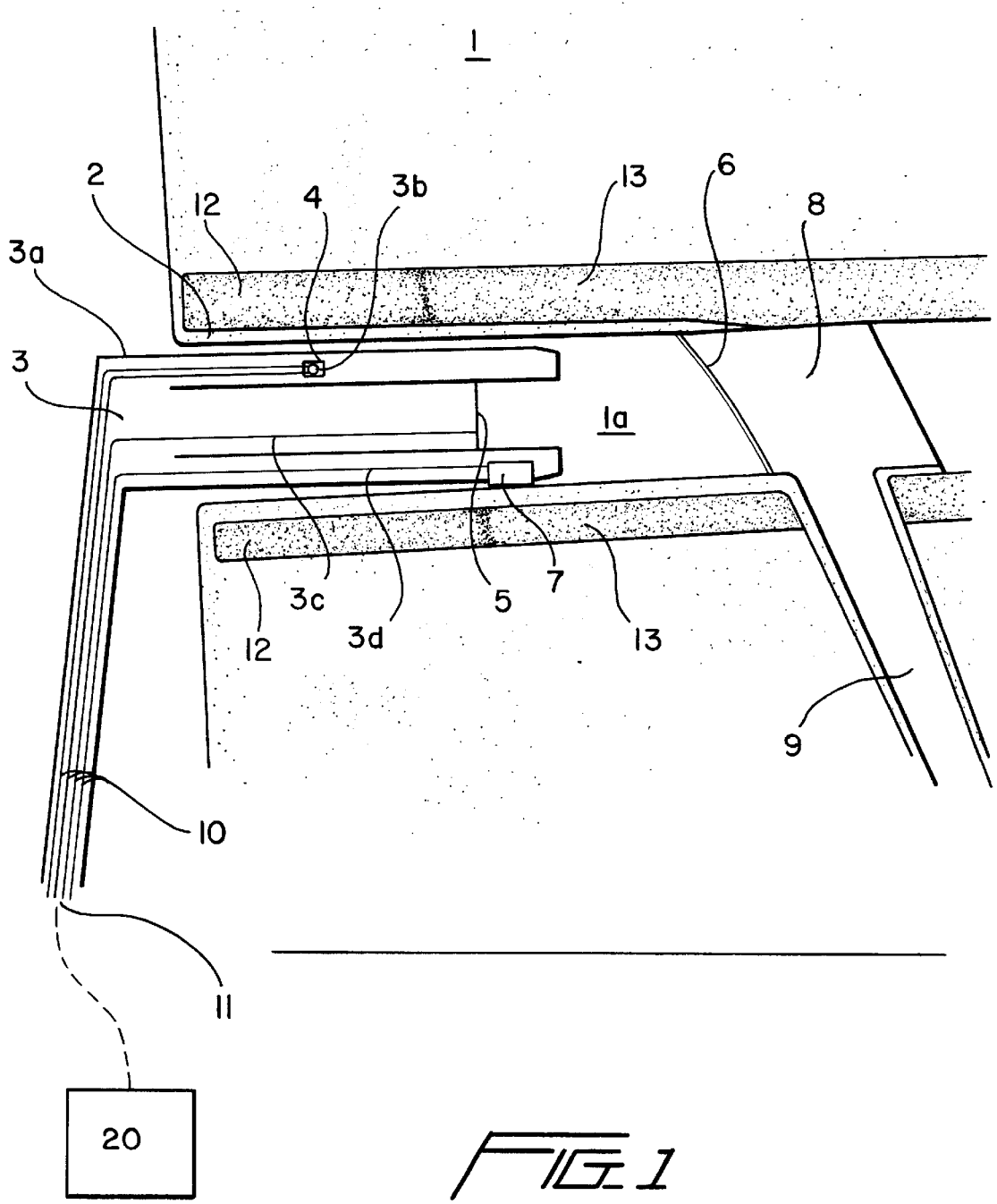
FIG. 1 schematically shows one embodiment of the intra aural probe of the present invention located in the ear canal with one configuration of sensors.

It was discovered that there is one anatomical site in the body which, with appropriate methods, can provide all of these vital signs measurements. This anatomical site is the external ear canal referred to as the external auditory meatus (E.A.M.). The E.A.M. is the portion of the ear which extends from the ear drum (tympanic membrane) to the ear lobe or pinna. The inner portion of the canal is part of the skull and is a bony tube lined with a rich supply of blood vessels and lining skin. The outer portion is made of cartilage with similar vessels and lining and attached hairs. The rich blood supply is believed to keep the air inside the canal close to body temperature for acoustic reasons. It is also relatively stagnant in terms of air movement and therefore reaches a steady state.

The ear drum itself separates the inner ear from the outer ear and is highly mobile or flaccid in one part. The inner ear is connected to the back of the nose via the Eustachian tube. The tube drains fluid from the ear to the back of the nose and opens to allow pressure changes to re-equilibrate across the drum. It is a relatively fluid connection between the drum and the region at the back of the nose called the nasopharynx.

It was discovered that the physical arrangement of the bony and cartilaginous canal makes it a unique place to measure blood flow and blood pressure. The blood flowing into the vessels lining the bony part of the canal come from the blood vessels supplying the underlying bone itself and is the only branch of the internal carotid artery which otherwise supplies only the brain. The cartilage portion is supplied from the facial artery supplying the skin of the face. The bone and cartilage are rigid and so the only way blood can flow into the vessel rich dermis is by expanding inward into the canal. It was recognised that if a semi rigid object, such as sound suppression ear plugs, is placed in the canal and the pulse pressure increased sufficiently, for example, by exercise, this pulsating expansion and contraction can be felt by the subject.

Both the heart rate and the pulse pressure can be measured by placing a suitable sensor in the canal to measure the movement or expansion of the lining skin. This can be accomplished be measuring the distance from one side of the canal wall to the other which shortens as the lining expands, or by placing a balloon in the canal and measuring the pressure directly. It can be measured also by occluding the outer part of the canal and measuring the pressure change inside the canal as the resistance to the pressure changes by the drum itself and the Eustachian tube are sufficient to permit a sensitive device to measure such changes. The changes are in the order of centimetres of water sufficient for many commercially available sensors.

The site also permits oxygen saturation measurement as the infra red light passes through the lining skin and reflects off the bone or cartilage below back to the detector. This signal can also be used to provide heart rate data and relative measure of the flow in the vessels. The blood flow in the deeper portion of the canal comes from the internal carotid itself and may therefore provide much more important information for a physician or nurse monitoring the patient.

Breathing in is produced by the diaphragm pushing down and sucking air into the lungs inside the chest. The vacuum produced is transmitted to the trachea and naso-pharynx. When a person breathes out the changes are reversed and there is a positive pressure produced in the trachea and naso-pharynx. It was discovered that these pressure changes are transmitted up the fluid connection of the Eustachian tube and across the ear drum. When the outer ear is occluded the pressure changes can be measured in the ear canal.

The present invention provides a method for monitoring multiple physiological parameters simultaneously, including:
  measuring blood pressure and pulse rate and volume of blood by detecting contraction and expansion in the vascular bed of the lining tissue of the external auditory canal during the cardiac cycle, and
  measuring respiratory rate and respiratory volume by detecting pressure changes across the tympanic membrane or movement of the tympanic membrane induced by corresponding pressure changes in the naso-pharynx and trachea during respiration.
Preferably, the method also includes:
  measuring temperature in the external auditory canal,
  measuring electroencephalographic voltages or electrocardiographic voltages by measuring small potential differences between the external auditory canal region and a suitable reference position outside,
  measuring electroencephalographic currents by measuring magnetic flux, and
  measuring changes in oxygen saturation of the haemoglobin travelling in the capillary bed lining the external auditory canal.

The present invention also provides an apparatus for monitoring multiple physiological parameters, including:
  a probe insertable into the external auditory canal, said probe having:
    a sensor for measuring blood pressure and pulse rate and volume of blood by detecting contraction and expansion in the vascular bed of the lining tissue of the external auditory canal during the cardiac cycle, and
    a sensor for measuring respiratory rate and respiratory volume by detecting pressure changes across the tympanic membrane or movement of the tympanic membrane induced by corresponding pressure changes in the naso-pharynx and trachea during respiration.
Preferably, the probe also includes:
  a sensor for measuring temperature in the external auditory canal,
  a sensor for measuring electroencephalographic voltages or electrocardiographic voltages by measuring small potential differences between the external auditory canal region and a suitable reference position outside,
  a sensor for measuring electroencephalographic currents by measuring magnetic flux, and
  a sensor for measuring changes in oxygen saturation of the haemoglobin travelling in the capillary bed lining the external auditory canal.

A single probe which measures pressure changes when placed in the ear canal can measure both the arterial pulse and respiration. The complex signal produced has both components but as they produce significantly different frequency and amplitude, they can easily be distinguished. Respiration is typically a slow sinusoidal wave around 12 cycles per minute. The arterial wave is more discrete pulse of smaller amplitude and commonly around 60 times per minute.

The same probe can have light emitting diodes or appropriately arranged fibre optic connections to measure the near infra red absorption at selected wavelengths and thereby determine the oxygen saturation. As the oxygenated blood enters the capillary bed the oxygen is removed and the light absorption changes. This is visible as a sinusoidal waveform in sync with the arterial pulse. This signal can be used to identify the arterial component of the combined pressure wave described above, to further enhance separation of the respiratory and arterial component.

In addition, the probe can have an optical or electric temperature sensing device incorporated to measure core temperature. The combination of sensors would provide at a single site all the information required to monitor a patent in many settings. In addition, the probe may have a speaker built in or acoustic signals transmitted through the pressure for communication. This would be useful in monitoring a subject for research or a pilot in flight. The ability to "put back" sound otherwise blocked out by the probe decreases the obtrusive nature of the probe itself.

In the following, the invention will be explained with reference to the drawings wherein:

Referring now to FIG. 1, one embodiment of the probe apparatus is shown, representing, a cut away view of part of the skull 1 through the external ear canal. An integrated sensor apparatus 3 is inserted into the ear canal 1*a* and seals against the lining skin 2 of the canal itself. The apparatus 3 has a peripheral wall 3*a* and is dimensioned to comfortably, but tightly, seal within the ear canal 1*a*. The peripheral wall 3*a* has a window 3*b* for receiving an end 4 of fibre optic cables 10. The apparatus 3 may generally be hollow and carries a pressure sensing diaphragm 5 which measures pressure changes within the ear canal 1a and supplies output signals by an electrical cable 3c. The peripheral wall 3a of the apparatus 3 also carries a temperature sensor 7 which is coupled to an electrical wire 3d. The lining skin 2 contains the rich vascular bed which expands and contracts with the cardiac pulse. The lining is contained within the canal 1a and lines either the cartilage portion 12 or bony portion 13 of the rigid tube which forms the canal. The integrated sensor apparatus 3 is inserted inside the canal 1a but does not come in contact with the ear drum 6 which anatomically and physically separates the outer ear canal from the middle ear 8. The middle ear 8 is in direct connection with the Eustachian tube 9 which transmits pressure changes from the back of the nose (not shown) to the middle ear 8. These pressure changes are produced during breathing in and out and are transmitted up the Eustachian tube 9 across the ear drum (pars flaccida) 6 and are measured by the pressure sensing diaphragm 5 held in the apparatus 3. The expansion of the vascular bed in the lining skin 2 increases the pressure inside the sealed canal 1a. Some of the pressure change is lost across the ear drum and into the Eustachian tube but because the pulse is rapid and short lived the resistance and inertia in the Ear drum and Eustachian tube permit the signal to be still measurable by a device capable of sensing pressure changes below a few centimetres of water.

The apparatus 3 itself may even have a minute hole to the outside (not shown) to permit slow equilibration of pressure over several seconds while not effecting detection of the pulse or respiratory movement. The hole has to be sufficiently small so as to act like a low pass frequency filter. The frequency of the measured signals being greater than what the "equalisation of pressure" would be. This would provide greater comfort to the wearer and decrease the risk of injury to the drum 6.

Figure 2:
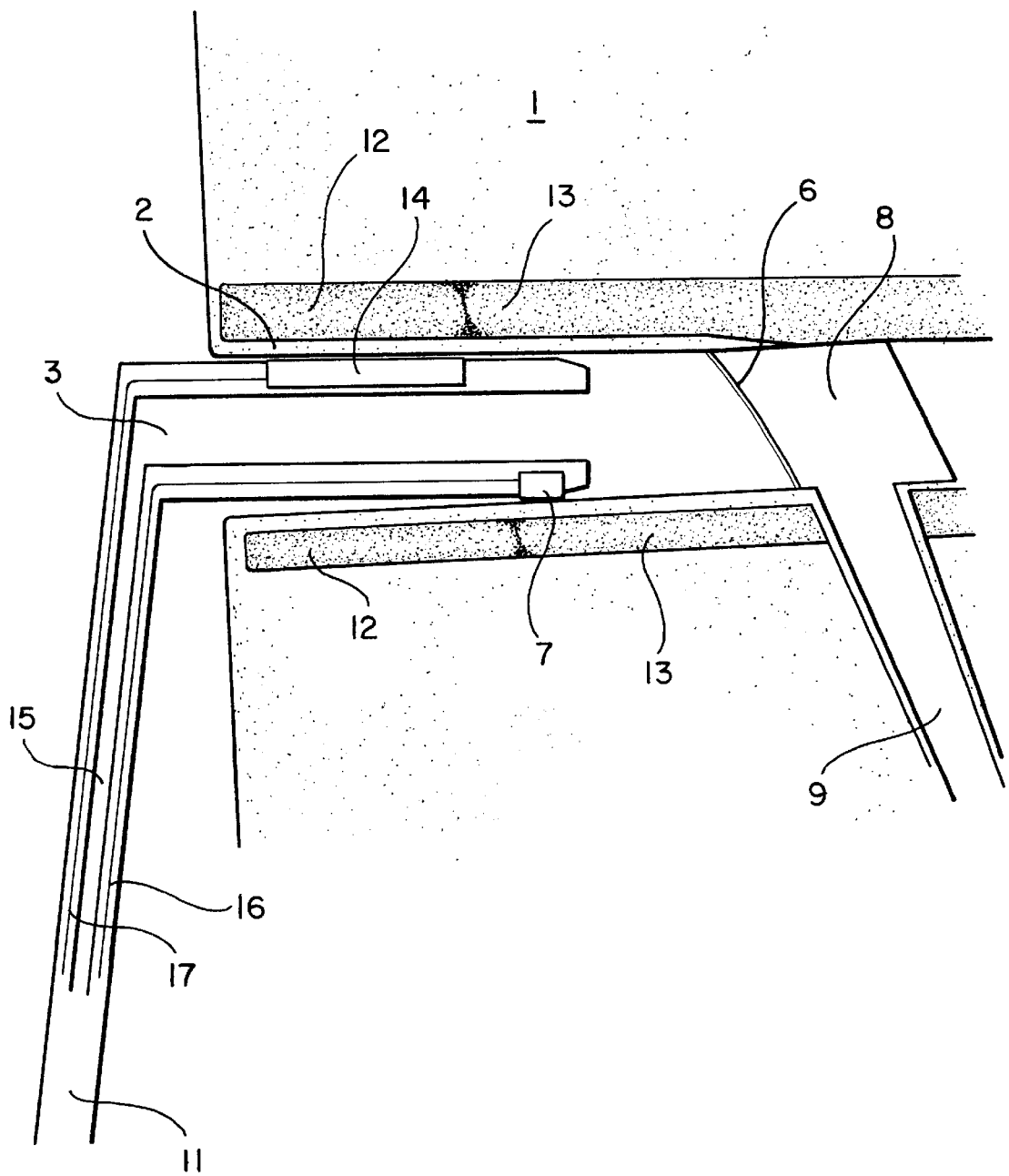
FIG. 2 schematically shows another embodiment of the intra aural probe of the present invention located in the ear canal with a second configuration of sensors.

For various reasons the direct incorporation of the near infra red spectroscopy system may be better performed in a larger space remote from the ear canal. This can be achieved by transmitting the incident and reflected light through fibre optic cables 10 via the window 3b. These cables 10 may be only microns in diameter and can be incorporated into a cable 11 carrying the electric wires 3c and 3d from the pressure sensor 5 and the temperature sensor 7 back to the main electronic signal processing, data collection, storage and presentation hardware 20. Referring now to FIG. 2, a second embodiment shows a variation in which the pressure wave is transmitted through flexible tubing 15. The infra red pulse oximetry is performed directly at the site by infra red light emitting diodes 14 and detecting transistors 14. The electrical signal from the infra red sensors 17 and the power supply (not shown) as well as the electrical wiring 16 carrying the signal from the temperature sensor 7 may be incorporated in the cable 11 carrying the flexible pressure tubing 15.

The operation of the device is essentially the same as for that described in FIG. 1 except that the pressure changes are transmitted physically to a sensor located at a remote site. In both systems, an acoustic signal can be injected into the probe to provide sound. The acoustic signal itself would be directly or electronically subtracted from the combined pressure signal so as not to interfere with the signal sensitivity. Both variations or combinations are possible and the final configuration is determined by such factors as the available size, components and costs.

The described arrangement has been advanced by explanation and many modifications may be made without departing from the spirit and scope of the invention which includes every novel feature and novel combination of features hereindisclosed.

Those skilled in the art will appreciate that the invention described herein is susceptible to variations and modifications other than those specifically described. It is understood that the invention includes all such variations and modifications which fall within the spirit and scope.

What is claimed is:

1. A method for monitoring multiple physiological parameters simultaneously, including, measuring blood pressure and pulse rate and volume of blood by detecting contraction and expansion in the vascular bed of the lining tissue of the external auditory canal during the cardiac cycle, and measuring respiratory rate and respiratory volume by detecting pressure changes across the tympanic membrane or movement of the tympanic membrane induced by corresponding pressure changes in the naso-pharynx and trachea during respiration.

2. The method of claim 1 further including:

measuring temperature in the external auditory canal, measuring electroencephalographic voltages or electrocardiographic voltages by measuring small potential differences between the external auditory canal region and a suitable reference position outside, measuring electroencephalographic currents by measuring magnetic flux, and measuring changes in oxygen saturation of the haemoglobin travelling in the capillary bed lining the external auditory canal.

3. A method as in claim 1 wherein the detecting of the expansion and contraction of the vascular bed measures pressure changes within the canal produced by said expansion and contraction.

4. A method as in claim 1 wherein the detecting of the expansion and contraction of the vascular bed measures the thickness of the vascular bed directly.

5. A method as in claim 1 wherein the detecting of the expansion and contraction of the vascular bed measures the distance between the opposing walls of the external auditory canal.

6. A method as in claim 1 wherein the detecting of the expansion and contraction of the vascular bed measures the volume within the external auditory canal.

7. A method as in claim 1 further including inserting a measurement probe into the external auditory canal of a patient to make said measurements.

8. An apparatus for monitoring multiple physiological parameters comprising:

a probe insertable into the external auditory canal, said probe having:

a sensor for measuring blood pressure and pulse rate and volume of blood by detecting contraction and expansion in the vascular bed of the lining tissue of the external auditory canal during the cardiac cycle, and a sensor for measuring respiratory rate and respiratory volume by detecting pressure changes across the tympanic membrane or movement of the tympanic membrane induced by corresponding pressure changes in the naso-pharynx and trachea during respiration.

9. An apparatus as in claim 8 wherein the probe further includes:

a sensor for measuring temperature in the external auditory canal,

- a sensor for measuring electroencephalographic voltages or electrocardiographic voltages by measuring small potential differences between the external auditory canal region and a suitable reference position outside,
- a sensor for measuring electroencephalographic currents by measuring magnetic flux, and
- a sensor for measuring changes in oxygen saturation of the haemoglobin travelling in the capillary bed lining the external auditory canal.

10. An apparatus as in claim 8 wherein the sensor for detecting the expansion and contraction of the vascular bed measures pressure changes within the canal produced by said expansion and contraction.

11. An apparatus as in claim 8 wherein the sensor for detecting the expansion and contraction of the vascular bed measures the thickness of the vascular bed directly.

12. An apparatus as in claim 8 wherein the sensor for detecting the expansion and contraction of the vascular bed measures the distance between the opposing walls of the external auditory canal.

13. An apparatus as in claim 8 wherein the sensor for detecting the expansion and contraction of the vascular bed measures the volume within the external auditory canal.

14. An apparatus as in claim 8 wherein the probe is coupled to processing means for receiving signals from said sensors and processing said signals to determine said physiological parameters.

15. An apparatus as in claim 8 wherein the probe is dimensioned to fit sealingly into the said external auditory canal.

* * * * *